United States Patent
Fischer et al.

(10) Patent No.: US 10,669,056 B2
(45) Date of Patent: Jun. 2, 2020

(54) METHOD FOR DISCHARGING AN OXIDISABLE COMPOUND IN THE LIQUID STATE

(71) Applicant: RHODIA OPERATIONS, Paris (FR)

(72) Inventors: Lars Fischer, Vienne (FR); Jacques Cavezzan, Villeurbanne (FR); Jean-François Thome, Vourles (FR)

(73) Assignee: Rhodia Operations, Paris (FR)

( * ) Notice: Subject to any disclaimer, the term of this patent is extended or adjusted under 35 U.S.C. 154(b) by 327 days.

(21) Appl. No.: 15/512,326

(22) PCT Filed: Sep. 15, 2015

(86) PCT No.: PCT/EP2015/071062
§ 371 (c)(1),
(2) Date: Mar. 17, 2017

(87) PCT Pub. No.: WO2016/041943
PCT Pub. Date: Mar. 24, 2016

(65) Prior Publication Data
US 2017/0275039 A1  Sep. 28, 2017

(30) Foreign Application Priority Data
Sep. 18, 2014 (FR) .................................. 14 58828

(51) Int. Cl.
*B65B 69/00* (2006.01)
*C07C 39/08* (2006.01)

(52) U.S. Cl.
CPC .......... *B65B 69/0066* (2013.01); *C07C 39/08* (2013.01); *B01J 2219/00094* (2013.01)

(58) Field of Classification Search
CPC .......................... B67D 3/0022; B65B 69/0066
See application file for complete search history.

(56) References Cited

U.S. PATENT DOCUMENTS

| | | | |
|---|---|---|---|
| 6,371,756 B1 | 4/2002 | Toohey | |
| 6,412,670 B1 | 7/2002 | Randmae et al. | |
| 6,517,057 B1 | 2/2003 | Aichinger et al. | |
| 2007/0253687 A1* | 11/2007 | Palkie | A45D 26/0014 |
| | | | 392/441 |
| 2016/0100604 A1* | 4/2016 | Rubin | A23G 1/20 |
| | | | 426/520 |

FOREIGN PATENT DOCUMENTS

| | | |
|---|---|---|
| EP | 0364850 A1 | 4/1990 |
| JP | 2010222328 A | 10/2010 |
| JP | 2013114096 A | 6/2013 |
| JP | 2014095816 A | 5/2014 |
| WO | 2007024023 A1 | 3/2007 |

* cited by examiner

Primary Examiner — Timothy P. Kelly

(57) ABSTRACT

A process for unloading a container containing an oxidizable compound having a melting point $T_m$ greater than 15° C. is described. This process comprises the steps consisting in heating the container using a heating means until the oxidizable compound is liquid, the temperature of the heating means remaining less than or equal to $T_m+105°$ C., and then unloading the oxidizable compound in the liquid state. A process for handling such an oxidizable compound, comprising this unloading step, and also a device enabling this process to be carried out, are also proposed.

9 Claims, No Drawings

METHOD FOR DISCHARGING AN OXIDISABLE COMPOUND IN THE LIQUID STATE

This application is a U.S. national stage entry under 35 U.S.C. § 371 of International Patent Application No. PCT/EP2015/071062, filed Sep. 15, 2015, which claims priority to French Patent Application No. 1458828, filed on Sep. 18, 2014, the whole content of each of these applications is hereby incorporated herein by reference for all purposes.

TECHNICAL FIELD OF THE INVENTION

The present invention relates to the handling of oxidizable products in the solid state at ambient temperature. More specifically, this invention relates to the step of unloading such a product in the liquid state, but also to the steps of loading, storage and transport.

PRIOR ART

Polymerization inhibitors are chemical compounds capable of preventing polymerization reactions between monomers. They are therefore compounds which are widely used in industry and are added to containers of monomers to facilitate and make safe the storage, transport or distillation thereof. Among these inhibitors, para-methoxyphenol (PMP) is a well-known compound, which is generally in the form of a solid, its melting point being approximately 55° C. However, in industry, a composition in liquid form may be preferred since it is easier to pump and mix compared to a solid form. However, a technical difficulty lies in the fact that PMP is sensitive to oxidation. Indeed, if left in an oxidizing medium, for example air, PMP in liquid form reacts and the by-products formed may be colored. Now, the coloring of the compound is a significant problem since it can also lead to the coloring of the polymer composition resulting from the polymerization of the monomer, which can be highly undesirable depending on the final applications for the polymer composition.

In U.S. Pat. No. 6,517,057, a system for dispensing a polymerization-inhibiting compound in a vessel of polymerizable material is described. This system, which has the advantage of being reliable and simple, is however only suitable for dispensing an inhibitor in liquid form, such as a solution of phenothiazine (PTZ) which is liquid at ambient temperature. This device is not suitable for the case in which the polymerization-inhibiting compound is in solid form. The use of inhibitor in solution is not desirable. Firstly, traces of solvent may remain undesirably in the monomer solutions. Secondly, transporting a compound in solution represents an extra expenditure of both energy and money which is not desirable in the context of sustainable development.

Patent application EP 0 364 850 describes a device for storing an air- or moisture-sensitive material in a container, and a process for unloading said material. This document describes in particular the use of heating plates to liquefy the air- or moisture-sensitive material. However, no indication is given as to the method of heating or the temperature of heating.

International application WO 2007/024023, for its part, describes a process for producing a material made of polyalkylene oxide resin, which comprises a step of heating the upper surface of the resin. The only indication regarding the way in which this heating is to be carried out is that the heating temperature must not exceed 300° C. which, for a resin with a melting point of between 0° C. and 60° C., is a very high limit.

It is in this context that the inventors have sought a process which enables a compound which is solid at ambient temperature to be unloaded, in the liquid state, without encountering problems of degradation and coloring of the compound. More generally, one of the aims is to propose a process for unloading an oxidizable compound having a melting point of greater than or equal to 15° C.

It is moreover desired that the unloading be easy to implement, that it not require any costly means, and that the quantity of product lost during the unloading be as low as possible, preferably negligible. Advantageously, it is also desired to avoid any risk of blocking the discharging equipment from the container to the tank for storage or use of the product.

DESCRIPTION OF THE INVENTION

A subject of the invention is a process for unloading a container containing an oxidizable compound having a melting point $T_m$ of greater than 15° C., comprising the steps consisting in:

a) heating the container using a heating means until the oxidizable compound is liquid, the temperature of the heating means remaining less than or equal to $T_m+105°$ C.;

b) unloading the oxidizable compound in the liquid state.

Another subject of the invention is a process for handling an oxidizable compound having a melting point $T_m$ of greater than 15° C., comprising the steps of loading a container with an oxidizable compound, of storage and/or transport of the loaded container, of unloading the container and optionally of returning the container after unloading, characterized in that the unloading step is carried out as described above.

Finally, a device comprising (A) a container which can be used in the processes described above and (B) instructions for unloading said container is also proposed here.

In the following description, the expression "between . . . and . . ." should be understood as including the mentioned limits.

The subject of the present invention is linked to the handling of an oxidizable compound having a melting point $T_m$ of greater than 15° C.

In the following description, the expression "oxidizable compound" means in particular a chemical compound which is liable to transform when it is placed in contact with an oxidizing medium, in particular a medium containing oxygen. The oxidizable compound according to the invention may be a compound which undergoes undesired degradation when it is placed in air. A consequence of this degradation may in particular be a color change or the formation of heavy compounds which may lead to a loss of product or deposition on the walls of the containers. It may be a compound which is oxidizable at ambient temperature or else at a temperature greater than ambient temperature, for example at a temperature to which the compound is subjected during its transport, storage or use. Compounds known for their high stability in air, such as candle waxes, are therefore not affected by the present invention.

The oxidizable compound according to the invention has a melting point (also referred to as melting temperature and denoted by $T_m$) of greater than 15° C. $T_m$ is preferably greater than 25° C., more preferably greater than 35° C. and even more preferably greater than 50° C. Advantageously, $T_m$ may be less than 200° C., more preferably less than 150°

C. and even more preferably less than 130° C. At ambient temperature, the oxidizable compound according to the invention is conventionally in the solid state. At ambient temperature, the contents of the container according to the invention is in the solid state. It is understood that the oxidizable compound is not in solution. According to the invention, the ambient temperature is defined by a temperature range generally of from 10° C. to 30° C., preferably from 15° C. to 30° C. and more preferably from 15° C. to 25° C. Nonetheless, the cases in which the oxidizable compound is subjected to more extreme ambient temperatures are not ruled out: the ambient temperature may, for example, in certain places in winter, reach −15° C. or −20° C. The ambient temperature may in this case be defined by a temperature range of from −20° C. to 10° C., preferably from −15° C. to 0° C.

The oxidizable compound according to the invention may be a pure compound or it is an oxidizable mixture having a melting point of greater than 15° C.

According to a preferred embodiment, the oxidizable compound according to the invention is a polymerization-inhibiting compound. Polymerization inhibitors are intended to prevent the polymerization of monomers, for example the free-radical polymerization of ethylenically unsaturated monomers, during the industrial preparation, storage and/or transport thereof. The polymerization-inhibiting compound may be a pure compound, a mixture of several compounds which are themselves polymerization inhibitors, or else a compound essentially composed of one or more polymerization-inhibiting compounds and additives, with the additives representing preferably less than 10% by weight, more preferably less than 5% by weight, and even more preferably less than 1% by weight of the total composition. Among the polymerization-inhibiting compounds, mention may be made of p-methoxyphenol, 4-tert-butylcatechol, pyrocatechol, hydroquinone, Topanol A (2,4-dimethyl-6-tert-butylphenol), phenothiazine, copper dibutyldithiocarbamate, benzoquinone and mixtures thereof. The oxidizable compound according to the invention may be a compound essentially composed of one or more polymerization-inhibiting compounds selected from the group consisting of p-methoxyphenol, hydroquinone and 4-tert-butylcatechol. Most particularly, the oxidizable compound according to the invention is essentially composed of p-methoxyphenol (denoted PMP).

Conventionally, polymerization-inhibiting compounds which have a melting point of greater than 15° C. such as PMP are produced in the solid form, for example in the form of powder, flakes, pellets, extrudates, spheres, beads or pastilles. They may also be in the liquid form if they are heated beyond their melting point. For their transport and storage, these oxidizable compounds may be packaged in containers, in particular when they are in the liquid state.

In the present invention, the oxidizable compound is contained in a container. In the present description, the term "container" includes drums, bottom-unloading containers, and mobile tanks with top unloading. This container may have any structure enabling it to carry out its function, and may be insulated or not. Preferably, the container according to the invention is a container of IBC (intermediate bulk container) type, as is well known in the technical field. Different types of containers are available in industry, for example from the manufacturers GLI, SCHÄFER or UCON.

The volume of the container according to the invention may be between 50 l and 10 000 l, more preferably between 500 l and 2500 l. According to one embodiment of the invention, the container is a small container, the volume of which is preferably between 500 l and 2000l.

The container may be constructed from coated steel, but preferably from stainless steel. When the container is adapted for bottom unloading, this preferably presents as little obstacle as possible to the flow of the product inside, and has a bottom with a special shape which promotes flow of the molten product. Various bottom valve technologies are possible. Preferably, a bottom butterfly valve can be chosen, arranged as close as possible to the bottom of the container to reduce any cold zone.

A heating means is used in the process according to the invention. This heating means may be selected from all the devices known to those skilled in the art which enable the temperature within the container to be modified. Just one or several identical or different heating means may be used simultaneously or alternately. The one or several heating means may be devices which are built into the container and which cannot be removed therefrom, or else removable devices which are connected to the container, or else devices which are separate from the container.

The container may be thermally insulated from the ambient environment by its own insulation, or by any device separate from the container and capable of carrying out this function.

According to a first embodiment, the container is equipped with a wall and preferably a bottom which have a jacket, in which a heat-transfer fluid can flow. The heat-transfer fluid may in particular be liquid water or steam.

According to another embodiment, the container is provided with heating resistors.

According to yet another embodiment, the heating means consists of a heating blanket or a heating shell which may be placed around the container when the latter is not insulated.

According to yet another embodiment, the container is provided with a heating pin or coil, in which a heat transfer fluid can flow.

According to yet another embodiment, the heating means consists of an oven or a hot chamber in which the container may be placed.

The invention relates to a process for unloading said container containing an oxidizable compound which has a melting point $T_m$ of greater than 15° C. This process comprises a first step a) which consists in heating the container using a heating means until the oxidizable compound is liquid, the temperature of the heating means remaining less than or equal to $T_m+105°$ C., preferably $T_m+70°$ C.

This step advantageously makes it possible to render the compound liquid enough to be unloaded from the container. In the present description, a compound can be considered to be liquid when its viscosity is advantageously less than or equal to 100 Pa·s, preferably 1 Pa·s, and more preferably 10 mPa·s, measured by means of a Rheomat 30 viscometer for shear rates of $100\ s^{-1}$ to $500\ s^{-1}$. The duration and temperature of heating are thus adapted so that this result is obtained. The duration and temperature of heating may depend on the physical form, the amount and the starting temperature of the oxidizable compound to be heated, and also on the presence of an insulation, the ambient temperature and the heating means used.

Generally, the duration of the step a) of heating may be between 1 hour and 10 days, more preferably between 2 hours and 5 days, and even more preferably between 4 hours and 48 hours. Preferably, when the temperature is chosen to be towards the lower end of the described range, then the duration is chosen to be towards the upper end of the range, and vice versa.

It may however be difficult to control the homogeneity of the heating within the container. The entirety of the compound can be considered to have reached the liquid state when the temperature of the compound, measured in the container, is greater than the melting point $T_m$ of the compound by at least 10° C., more preferably by at least 20° C., for a duration of at least 2 hours, preferably at least 5 hours, and more preferably at least 8 hours. The temperature of the oxidizable compound at the end of the step a) of heating is preferably at most $T_m+100°$ C., more preferably $T_m+65°$ C. The temperature of the oxidizable compound inside the container may for example be measured by means of a removable or non-removable pyrometer tube in a protective thimble, or else by means of any contacted or contactless temperature sensor arranged permanently or non-permanently on the container. This criterion relating to the temperature of the compound is preferably fulfilled at at least one point within the container, preferably at at least two points within the container and even more preferably at at least three points within the container. These points may be chosen in the central part of the container, towards the walls or close to the outlet valve. The inventors have nonetheless noted that the heating of the oxidizable compound could have the effect of degrading the compound. They have therefore discovered that, to avoid local overheating of the oxidizable compound, the heating step should be carried out in such a way that the temperature of the heating means remains permanently less than or equal to a certain temperature. According to the present invention, during the step a) of heating, the temperature of the heating means remains less than or equal to $T_m+105°$ C., and preferably $T_m+70°$ C., $T_m$ being the melting point of the oxidizable compound. In this way, the temperature of the heated walls of the container in contact with the oxidizable compound remains less than or equal to $T_m+105°$ C., preferably $T_m+70°$ C.

Carrying out step a) of heating depends in particular on the heating means used and the nature of the fluids or mixture of fluids employed. Controlling the temperature of the heating means may be carried out in a known way by a person skilled in the art as a function of the type of heating means used. For example, when the heating means consists of a heat-transfer fluid flowing through a jacket or a coil, the temperature of the heating means can be controlled via the temperature of the heat-transfer fluid. When the heating means consists of an electrical device, the temperature of the heating means may be controlled via the electric power supply. When the heating means consists of an oven or a hot chamber, the temperature of the heating means may be controlled via a thermostat that sets the temperature of this oven or hot chamber. According to one embodiment, the container is provided with a jacket and step a) of heating consists in causing water between approximately 75° C. and approximately 95° C. or expanded steam between approximately 100° C. and approximately 160° C. to flow in the jacket of the container for a duration determined as a function of the ambient temperature and of the state of solidification of the product in the container.

According to a specific embodiment, the oxidizable compound having a melting point $T_m$ of greater than 15° C. is p-methoxyphenol and step a) consists in heating the container using the heating means until the oxidizable compound is liquid, the temperature of the heating means remaining less than or equal to 160° C., preferably less than or equal to 125° C. Preferably, the temperature of the oxidizable compound at the end of the heating step is between 65° C. and 155° C., more preferably between 75° C. and 120° C.

According to one particularly advantageous embodiment, step a) is carried out under an inert atmosphere.

In the following description, the expression "inert atmosphere" denotes in particular any gas with an oxygen content lower than that of air. The inert atmosphere is composed of a gas which may be selected from the group consisting of nitrogen, argon, depleted air and the mixture of these. The expression "depleted air" denotes air containing less than 20% oxygen. Preferably, step a) is carried out under nitrogen. Preferably, the inert atmosphere has a low moisture content, for example a moisture content below 1000 ppm of water. Preferably, it is industrial nitrogen.

For step a) to be carried out under an inert atmosphere, the container may be pre-inertized before it is filled, and during the heating thereof it may be connected, by its vent, to an inlet for low-pressure inert gas.

At the end of step a) of heating, the oxidizable compound in the liquid state is unloaded from the container. The unloading may be carried out by any appropriate technique, in particular as a function of the container's equipment. The unloading may for example be carried out from the top of the container or from the bottom of the container, either by gravity discharging or pressurized discharging or by pumping or by an ejector system. The unloading may be total or partial.

During the unloading, the oxidizable compound is transported from the container to another receptacle. According to one embodiment, this may be a vessel or a reactor containing a monomer or polymer composition. According to another embodiment, it may be another container, for example a container of smaller or larger volume.

Preferably, the unloading is carried out under an inert atmosphere. For this, the container may be connected, by its vent, to an inlet for dry inert gas. According to one embodiment, the container and the other receptacle into which the oxidizable compound is unloaded constitute a closed system. This embodiment is advantageous when it is not desired for the oxidizable compound to be placed in contact with an uncontrolled atmosphere, or else if the other receptacle into which the oxidizable compound is unloaded moreover contains a compound which is not desired to be placed in contact with an uncontrolled atmosphere.

Steps a) and (b) according to the invention may be carried out in the same place or in different places. In addition, these steps may be performed one after the other or not. When these steps are not performed one after the other, the duration between the end of step a) and the start of step (b) may be between 5 minutes and several days, for example 2 days. Indeed, when the oxidizable compound has reached the liquid state at the end of step a), it may retain this state for a certain duration, without regulating the temperature. This duration may depend in particular on the type of container and on its thermal insulation. It will be ensured that the compound is still in the liquid state during step (b) of unloading.

The liquid and gas connecting means between the container and the unloading receptacle are preferably as short as possible and are preferably insulated by any means enabling heat losses to be reduced.

The unloading process as described above advantageously makes it possible to solve the technical problems which may be encountered during the unloading, in the liquid state, of oxidizable material which is solid at ambient temperature. In particular, this unloading procedure makes it possible to avoid coloring the polymerization-inhibiting compounds such as PMP.

This unloading process may be associated with other handling steps such as loading and transport. This is why a subject of the present invention is also a process for the handling of an oxidizable compound having a melting point $T_m$ of greater than 15° C., comprising the steps:

of loading a container with an oxidizable compound,
of storage and/or transport of the loaded container,
of unloading the container,
and optionally of returning the container after unloading,
characterized in that the unloading step is carried out according to the process described above.

Loading the container with the oxidizable compound may be carried out by any appropriate technique, in particular as a function of the type of container and the physical form of the compound. The oxidizable compound may be loaded into the container in liquid form or solid form, preferably in liquid form at a temperature of greater than $T_m$. This process is advantageous in so far as the compound does not need to be shaped when leaving its production line. During the loading step, the container may be heated or cold.

The loading may be carried out without any particular precautions. However, loading in a closed system, that is to say without the oxidizable compound being in contact with the ambient atmosphere, may be preferable for reasons of health and safety and for preventing the degradation of the oxidizable compound. In this configuration, the vent is preferably heated to avoid any risk of sublimation of the product.

Moreover, the loading may be carried out under an inert atmosphere. For this, an inert gas may be injected into the container during and/or just after and preferably before the oxidizable compound is loaded. Before loading, the container may be filled with an inert gas. During loading, the inert atmosphere may be maintained by virtue, for example, of flushing with inert gas. Finally, just after the loading, an inert gas blanket may be created or maintained.

According to one preferred embodiment, the process for loading a container with an oxidizable compound having a melting point $T_m$ of greater than 15° C. comprises the steps consisting in:

placing the container under an inert atmosphere;
loading said oxidizable compound in the liquid state into the container.

This loading process may be a subject of the present invention. According to one preferred embodiment, the oxidizable compound is loaded into the container in the liquid state under an inert atmosphere.

Once loaded into the container, the oxidizable compound can be stored and/or transported. Preferably, the temperature of the container is not regulated during the step of storage and/or transport, which enables a cost reduction. Under normal conditions, if the container is not maintained at a temperature greater than the melting point $T_m$ of the oxidizable compound, the compound will solidify inside the container. The duration necessary for the compound to be in the solid state in the container may vary as a function of the nature of the compound, type of container, ambient temperature and the conditions of storage and/or transport. Very generally speaking, the compound may take from 2 to 8 or 10 days to take a solid form.

During storage and transport, all openings in the container preferably remain hermetically sealed.

Once at its point of unloading, a person skilled in the art may carry out the unloading procedure according to the present invention for easily and efficiently unloading the oxidizable compound in the liquid state, without degrading the compound.

After the total or partial unloading of the container, the latter may be transported to its starting point to be optionally reused. According to one preferred embodiment, after unloading the container is put or maintained under an inert atmosphere, then returned under an inert atmosphere. This is particularly advantageous if some oxidizable compound is still in the container. This is also advantageous if the container is then reused, the initial step of inertizing the container then having already been carried out.

Another subject of the invention is a device that makes it possible to carry out the unloading process described above, and also the handling process described above. This device comprises:

(A) a container, optionally provided with a heating means, which can be used in the process according to the invention, and
(B) instructions for unloading said container in accordance with said process.

The container (A) may be as described with preference above. In particular, the container may preferably be provided with at least one heating means, and said heating means is selected from a device which is built into the container and which cannot be removed therefrom, a removable device which is connected to the container, or else a device which is separate from the container. The instructions (B) describe the steps which have to be carried out in order to unload the container (A) according to the invention. Moreover, these instructions may describe preferred embodiments, and also other handling steps such as loading, storage, transport and returning the container. Preferably, these instructions are in written form on a paper support, but it is also possible for them to be recorded on an electronic support, in written, audio or video form.

The invention will be explained in more detail by means of the examples hereafter given by way of nonlimiting illustration.

EXAMPLES

Example of Heating with Hot Water

A 1000 kg stainless steel container was filled with molten PMP and the container was insulated. When the temperature of the product in the container reached 28° C., the PMP was then in the solid state in the container. The container was placed under an inert atmosphere. The container was heated by causing hot water at a temperature of 70° C. to flow in the jacket of the container for a duration of 4 days under nitrogen. At the end of this heating, the product obtained was fluid and homogeneous and the container was discharged by gravity into a storage container. The product had a coloring of less than 100 Hazen units.

This procedure was reproduced, but without intertizing the container. The container was then heated with hot water at 70° C. under air for a duration of 4 days. The product obtained was fluid and had, after discharging, a coloring of 220 Hazen units.

For comparison, this procedure was reproduced but the heating step lasted only 20 hours. The product obtained was fluid but not homogeneous and had agglomerates of solid PMP. After discharging, the container was weighed and there was 130 kg of solid PMP inside the container.

Example of Heating with Steam at 140° C.

A 1000 kg stainless steel container was filled with molten PMP and the container was insulated. When the temperature of the product in the container reached 28° C., the PMP was then in the solid state in the container. The container was placed under an inert atmosphere. The container was heated with steam at 140° C. under nitrogen for 24 hours. The product obtained was fluid and homogeneous. The container was discharged by gravity. The product had a coloring equal to 100 Hazen units.

This procedure was reproduced, but without intertizing the container. The container was heated with steam at 140° C. under air for 24 hours. The product obtained was fluid and had, after discharging, a coloring equal to 150 Hazen units.

For comparison, this procedure was reproduced but with heating of the container with 6 bar steam with a wall temperature of 165° C. under air for 24 hours. The product obtained was fluid and had, after discharging, a coloring greater than 300 Hazen units.

Example of Heating with Expanded Steam at 100° C.

A 1000 kg stainless steel container was filled with molten PMP and the container was insulated. When the temperature of the product in the container reached 28° C., the PMP was then in the solid state in the container. The container was placed under an inert atmosphere. The container was heated with expanded steam at 100° C. under nitrogen for 24 hours. The product obtained was fluid and homogeneous and the container was discharged by gravity. The product had a coloring equal to 60 Hazen units.

The invention claimed is:

1. A process for unloading an oxidizable compound having a melting point $T_m$ of greater than 15° C. from a container, comprising:
   a) heating the container using heating means that remains at a temperature of less than or equal to $T_m+105°$ C. until the oxidizable compound is in the liquid state; and
   b) unloading the oxidizable compound in the liquid state, wherein the oxidizable compound comprises one or more polymerization-inhibiting compounds.

2. The process as claimed in claim 1, wherein the heating is carried out under an inert atmosphere.

3. The process as claimed in claim 1, wherein the oxidizable compound comprises one or more compounds selected from the group consisting of p-methoxyphenol and 4-tert-butylcatechol.

4. The process as claimed in claim 3, wherein the oxidizable compound comprises p-methoxyphenol.

5. The process as claimed in claim 1, wherein all the oxidizable compound is in the liquid state when the temperature of the oxidizable compound, measured at at least one point in the central part of the container, is greater than the melting point $T_m$ of the oxidizable compound by at least 10° C., for a duration of at least 2 hours.

6. The process as claimed in claim 1, wherein the container is provided with a jacket and the heating comprises causing water at a temperature of between about 75° C. and about 95° C. to flow in the jacket.

7. The process as claimed in claim 1, wherein the container is provided with a jacket and the heating comprises causing expanded steam at a temperature of between about 100° C. and about 160° C. to flow in the jacket.

8. The process as claimed in claim 1, wherein the oxidizable compound comprises p-methoxyphenol, the temperature of the heating means remains less than or equal to 160° C., and the temperature of the oxidizable compound in the liquid state is between 65° C. and 155° C.

9. The process as claimed in claim 8, wherein the oxidizable compound comprises p-methoxyphenol, the temperature of the heating means remains less than or equal to 125° C., and the temperature of the oxidizable compound in the liquid state is between 75° C. and 120° C.

* * * * *